United States Patent [19]
Ponsford et al.

[11] Patent Number: 5,502,263
[45] Date of Patent: *Mar. 26, 1996

[54] METHOD OF RECLAIMING STYRENE AND OTHER PRODUCTS FROM POLYSTYRENE BASED PRODUCTS

[76] Inventors: Thomas E. Ponsford; Henry T. Ponsford, both of 14112 Durhullen Dr., Poway, Calif. 92064

[ * ] Notice: The term of this patent shall not extend beyond the expiration date of Pat. No. 5,406,010.

[21] Appl. No.: 370,682

[22] Filed: Jan. 10, 1995

Related U.S. Application Data

[63] Continuation of Ser. No. 10,350, Jan. 28, 1993, Pat. No. 5,406,010.
[51] Int. Cl.⁶ .................................................. C07C 4/04
[52] U.S. Cl. .......................... 585/241; 585/240; 585/439
[58] Field of Search ................................. 585/241, 240, 585/439

[56] References Cited

U.S. PATENT DOCUMENTS

3,692,858  9/1972  Brewer et al. ..................... 585/241
3,985,820  10/1976 Albright et al. ..................... 208/130
4,375,570  3/1983  Yudovich ............................ 585/241
5,288,934  2/1994  de Broqueville ................... 585/240
5,406,010  4/1995  Ponsford et al. ................... 585/439

Primary Examiner—Anthony McFarlane
Attorney, Agent, or Firm—Dain & Li

[57] ABSTRACT

In the method for reclaiming styrene monomer from polystyrene, polystyrene is mixed with a solvent and heated to approximately 300° C. to 400° C. to depolymerize the polystyrene to produce a styrene monomer fraction and a heavier fraction of partial depolymerization products. The styrene fraction is separated from the heavier fraction to recover the styrene monomer and polystyrene partial depolymerization products. In a preferred embodiment, the solvent comprises a "styrene oil" which results from the incomplete depolymerization of polystyrene, at least a portion of which is recycled to mix with polystyrene. The method is useful in reclaiming styrene monomer from napalm, foamed polystyrene, and other polystyrene products. In the case of reclamation of napalm, the method also includes the steps of separating and recovering benzene and gasoline.

6 Claims, 3 Drawing Sheets

METHOD OF RECLAIMING STYRENE AND OTHER PRODUCTS FROM POLYSTYRENE BASED PRODUCTS

This is a continuation of application Ser. No. 08/010,350, filed Jan. 28, 1993, now U.S. Pat. No. 5,406,010.

BACKGROUND OF THE INVENTION

1. Field of the Invention

This invention relates generally to recycling of polystyrene based products, and reclamation of styrene monomer from products containing polystyrene. The invention more particularly concerns a method for depolymerizing polystyrene producing a yield of styrene monomer and other useful polystyrene depolymerization by-products.

2. Description of Related Art

Polystyrene is a thermoplastic resin that is useful in many applications, for packaging, thermal and electrical insulation, fast food takeout containers, egg cartons, cups, coolers, and a variety of other types of containers and packaging products. Polystyrene is available as foam, also sold under the trademark "Styrofoam," owned by the Dow Chemical Co., which is useful for thermal insulation in light construction, such as for boats or trailer homes or the like, and in the form of foam beads, spheres or other shapes which are useful in packing. Polystyrene is also injection molded in the manufacture of toys, furniture, and medical products such as petri dishes and bioassay equipment. Because of the large amount of such forms of polystyrene which is largely discarded, it would be useful to provide a method of recycling such common commercial polystyrene products.

Polystyrene is also a major ingredient of napalm, which is a solution of polystyrene in benzene and gasoline. Recycling of the large existing military weapon stores of napalm by distillation of benzene and gasoline to yield polystyrene presents a number of dangers and difficulties, which has heretofore made this direct approach to reclaiming polystyrene from napalm inefficient and largely impractical. When dissolved in solvents such as benzene and gasoline and boiled, polystyrene acts as an effective foaming agent. In addition, a solution of polystyrene in such solvents is generally highly viscous, and has a low coefficient of heat transfer. When napalm reaches approximately 40° C., the lighter fractions of gasoline begin to boil off, and at approximately 80° C., the benzene boils. The free escape of benzene and gasoline gases being distilled from napalm is inhibited by the high viscosity of the solution, which becomes increasingly viscous as the solvents are distilled out of the solution. The boiling napalm can create a heavy foam, also referred to herein as the "soufflé effect." This foam can extrude into exits of the distillation apparatus, where the foam can cool, forming a solid polystyrene, blocking the exits and allowing pressure and temperature within the distillation apparatus to build up dangerously.

A "soufflé effect" from heavy foaming can also occur at a later stage in distillation when all of the benzene and light gasoline components have evaporated from the solution, leaving heavier gasoline components to boil off through a more viscous solution at only a slightly higher temperature. High viscosity further inhibits convective mixing and uniform heating, so that destructive "hot spots" can occur at the interface of the liquid with the surface of the distillation apparatus.

The heavy foaming which can occur during distillation of napalm can be reduced to some extent by the use of expensive and complex high pressure distillation systems or by distilling slowly. However, polystyrene also undergoes a degree of depolymerization not only as a function of temperature, but also as a function of the duration of exposure to elevated temperatures, producing styrene monomer and partial depolymerization products which are unacceptable in recovered polystyrene plastic. Some formulations of gasoline contain high boiling point fractions similar to kerosene. At high temperature, these fractions can react with the polystyrene plastic to form compounds which have disagreeable odors, and are therefore unacceptable contaminants in recycled polystyrene plastic. Driving out the residual gasoline fractions by further elevation of temperatures only causes more rapid depolymerization of the polystyrene plastic and further contamination of the polystyrene plastic by partial depolymerization products.

In view of the difficulty of extracting clean polystyrene intact from napalm, it would be advantageous to depolymerize the polystyrene to yield styrene monomer, which is a useful end product, and which can be easily recovered at commercial purity. Such a process would be useful for recovering styrene monomer from polystyrene products, such as foamed polystyrene, solid polystyrene, and napalm. One conventional process provides for depolymerizing polystyrene in a solvent such as benzene, having a boiling point substantially different from that of styrene, under temperature conditions of 350° C. to 600° C., but in sufficiently small quantities and the shortest possible amount of time, preferably less than one minute, to avoid production of high boiling point oils, considered in that process to be undesirable contaminants, and other undesirable byproducts. The styrene production rate of that process is therefore uneconomically low.

It would be desirable to provide a simple fractional distillation method requiring no pressure vessels or piping and no complex separation equipment to permit the reclamation of large quantities of styrene monomer from polystyrene based materials such as napalm or foamed styrene products. It would also be desirable to provide a process for reclaiming styrene monomer from such polystyrene materials that would prevent the occurrence of the heavy foaming "soufflé effect", and that would avoid contamination of the yield by residual fractions.

The recycling and reclamation of foamed polystyrene plastic has further presented a serious environmental challenge in recent years. Although some recycling of large, clean pieces of polystyrene foam is currently performed by cutting them into small pieces suitable for use as packing materials, there is limited demand for this type of recycled foamed polystyrene, and much waste polystyrene currently goes unreclaimed. A further problem is presented by the extremely low density of polystyrene foam, such that a whole truckload of polystyrene foam hardly weighs enough to pay for transportation to a reprocessing plant.

It would also be desirable to provide a process that greatly increases the density of the polystyrene material to be recycled, at the places of collection sites, to allow economical transportation of the collected polystyrene in sufficient quantity and density to allow conversion of the material into usable, salable materials. In addition, the reclamation process should be able to accept large and small pieces of polystyrene, and to tolerate some foreign matter, water and dirt mixed in with the plastic to be reclaimed. The present invention meets these needs.

SUMMARY OF THE INVENTION

Briefly, and in general terms, the present invention provides for a method for recycling and reclaiming polystyrene from such materials as napalm, polystyrene foam, and other polystyrene products by depolymerizing the polystyrene to yield styrene monomer and high boiling depolymerization products, without creating the heavy foaming "soufflé effect", and without contamination of the products by residual contaminants.

The invention accordingly provides for a method for reclaiming styrene monomer from polystyrene. The polystyrene is mixed with a solvent to form a polystyrene solution, which is heated to approximately 300° C. to 400° C. to depolymerize the polystyrene to produce a styrene monomer fraction and a heavier fraction of partial depolymerization products. The styrene fraction is then separated from the heavier fraction to recover the styrene monomer and polystyrene partial depolymerization products. In a preferred embodiment, the method includes the step of recycling at least a portion of the solvent to mix with polystyrene. The method is useful in reclaiming styrene monomer from napalm, foamed polystyrene, and other polystyrene products. In one preferred embodiment, the solvent advantageously comprises the partial depolymerization "styrene oil" products which result from the depolymerization of polystyrene according to the process of the invention. In the case of reclamation of napalm, the method also includes the steps of separating and recovering benzene and gasoline from the napalm mixture.

The method of the invention is advantageous in that it is relatively simple and can be operated at a relatively low cost. The method requires no pressurized vessels or piping, and no complex separation equipment, involving a simple fractional distillation, requiring only simple process instrumentation and controls, and allows for greater safety and reliability. The method produces no foaming "soufflé effect" due to the use of a relatively high boiling point solvent to maintain low viscosity during the depolymerization process. The method produces a high yield of styrene monomer and a "styrene oil" liquid mixture of relatively non-toxic organic compounds deriving from incompletely depolymerized polystyrene, resembling diesel fuel in appearance, viscosity, and boiling point, which can be recycled for use as the solvent in the process of the invention, and which can be used as a fuel oil.

Whereas in conventional depolymerization technology the high boiling point oils are considered to be "undesirable" contaminants which must be suppressed, in the present invention the high boiling point oils are recognized as easily separable substances which are highly useful, both in the execution of the process and for other uses, as will be discussed later.

These and other aspects and advantages of the invention will become apparent from the following detailed description, and the accompanying drawing, which illustrates by way of example the features of the invention.

DETAILED DESCRIPTION OF A PREFERRED EMBODIMENT

Conventional approaches to recycling and reclamation of polystyrene products have encountered problems of a heavy foaming "soufflé effect" due to the natural activity of polystyrene as an effective foaming agent. In addition, end products of polystyrene reclamation by either distillation or depolymerization have suffered from contamination from solvents or partial depolymerization byproducts.

The method of the invention for reclaiming styrene monomer from polystyrene based materials overcomes these problems, and can be applied to a wide variety of polystyrene products, foamed polystyrene, and polystyrene mixtures and solutions, such as napalm. Because the application to processing of napalm is representative of the more complex applications of the procedure, the method of the invention will first be described with regard to reclamation of napalm, and the method as applied to recycling and reclamation of polystyrene foam and other polystyrene products will be described later.

The stockpile of napalm weaponry in the United States is currently extensive, encompassing 23,000,000 pounds of the chemical solution of polystyrene, gasoline and benzene. Napalm typically consists of approximately 33 percent gasoline, 21 percent benzene, and 46 percent polystyrene, by weight. The gasoline utilized may contain compounds of sulfur, tetraethyl lead and other anti-knock derivatives. The napalm bombs are an excellent illustration of the versatility of the invention, as the distilled products of the invention can be used to solve the serious problem of cleaning the napalm out of the bomb casings. Napalm is a viscous fluid similar to honey; it can be poured out of the casing slowly, leaving behind a thick layer clinging to the inner wall of the casing. This residue must be removed from the casing, since it contains toxic benzene. Fortunately, both napalm and polystyrene are readily soluble in the fraction of gasoline which boils between 130° C. and 150° C. (described here as "medium gasoline"), especially if the medium gasoline is hot. The medium gasoline fraction can be separately condensed during the napalm distillation, as will be described in a later section. Since benzene boils at 80° C., it will not be found in significant amounts in the medium gasoline, which will thus have a low toxicity. A draining and cleaning fixture can be designed which will screw into the filler hole of the bomb casing, and will allow most of the napalm to drain into a collecting tank through a hose connected to the fixture, when the filler hole is turned downwards. This draining process is thus accomplished without allowing the toxic benzene to escape into the environment. Hot medium gasoline can then be sprayed through the fixture into the interior of the bomb casing to dissolve and wash out the dregs of the napalm into the same napalm collecting tank. If desired for maximum cleanliness, steam can then be sprayed into the bomb casing through the same fixture to evaporate and wash the dregs of the medium gasoline into the collecting tank, leaving the bomb casing interior "steam cleaned".

A special advantage of this cleaning process is its complete integration into the napalm distillation process. The cleaning solvents, water and medium gasoline, are distilled along with the napalm, condensed at the appropriate temperatures, and recirculated into holding tanks for reuse as cleaning solvents. Thus a truly infinite supply of regenerated cleaning solvents is readily available to remove the napalm from the many casings, all without exposure or leakage to the environment.

A second and possibly more important special advantage of this cleaning process is its ability to clean out bomb casings which have suffered small leaks through corrosion. The government estimates that possibly ten percent of the 35,000 casings have small leaks. In these casings, some of the most volatile fractions of the napalm solvents (light gasoline and benzene) have evaporated over time through the casings leaks, allowing the napalm to thicken into a solid mass, similar to a tube of model airplane glue when the cap is inadvertently left off for a long time. These casings are considered by the government to be an especially difficult recycling problem, but they are easily cleaned by means of this invention. Since the solidified napalm, which is merely polystyrene with a reduced level of solvents, is as soluble in hot medium gasoline as is pure polystyrene, and will even melt if the temperature of the hot medium gasoline exceeds 120° C., it is only necessary to continue the spray of hot medium gasoline into the casing for a longer time than usual, until all of the solidified napalm is dissolved or melted and washed out of the casing. Completion of the removal of solid napalm can be verified by ultrasonic diagnostics, or possibly simply by tapping the casing with a small hammer. The extra usage of medium gasoline solvent for the solidified bombs causes no problem, since it is easily regenerated around the distillation loop. As will be illustrated later, this integration of the solvents into the distillation process is also useful in the commercial collection and processing of discarded foamed polystyrene. After the napalm has been removed from the bomb casings, the casings can be recycled as scrap metal.

It has been found that in the method of the invention, essentially no gases, solids or char, and only 1% tar are produced from the depolymerization of polystyrene, and that polystyrene, at least under the conditions practiced in the process of the invention, appears to depolymerize substantially completely to liquids. In the process of heating napalm to a depolymerization temperature of approximately 350° C., a single fractional distillation produces first a mixture of benzene and gasoline, then a mixture of styrene monomer and another mixture defined herein as "styrene oil", that consists essentially of a mixture of about 20 high-boiling point, relatively non-toxic organic compounds deriving from incompletely depolymerized polystyrene, according to the process of the invention. The mixture resembles diesel fuel in appearance, viscosity, and boiling point, and is useful as a fuel oil. The "styrene oil" mixture has a pour point below −20° C., and boils between about 300° C. and about 320° C. at one atmosphere pressure. The "styrene oil" mixture distills to dryness at approximately 320° C. During boiling it will not self-ignite in air, and when used as a fuel oil, the burner must pre-mix the styrene oil mixture as a vapor with hot air to ensure smokeless burning. "Styrene oil" is a material with an unusual combination of properties, which appears to be chemically stable (it does not polymerize or thicken in times greater than one year), and is a good lubricant.

In order to prevent the "soufflé effect" during depolymerization of polystyrene, and to permit free boiling across the entire temperature range through the process of depolymerization and distillation, "styrene oil" is preferably added as a solvent to maintain low viscosity in the boiling polystyrene mixture. The solvent thus helps to allow easy escape of boiled gases and constant natural churning of the polystyrene mixture, permitting good convective heat transfer and avoiding hot spots at the walls of the depolymerization still. The practical process requirements for such a solvent are as follows:

1. Using a modest amount of the solvent (from about ½ to ⅔ of the weight of napalm), a solution of the solvent and napalm should have, at about 40° C., a viscosity low enough to permit benzene and gasoline to boil off freely without foaming.

2. After the benzene boils off, the viscosity of the remaining solution should remain low enough to enable the remaining gasoline to boil off freely.

3. At the highest boiling point of any gasoline fraction, the viscosity of the remaining solution of polystyrene in the solvent should remain low enough to enable the last of the heavier gasoline fractions to boil off freely. No solvent should have boiled away at this temperature.

4. As the temperature is elevated further, the polystyrene begins to depolymerize at the surface of the depolymerization still, and the viscosity at this stage should be low enough to permit the styrene monomer and the "styrene oil" mixture to boil off freely. The solvent also should not inhibit the depolymerization process.

5. Although it is permissible for some of the solvent to begin to evaporate before the polystyrene depolymerization is complete, the solvent should have a high enough boiling point to allow all of the polystyrene to depolymerize in the presence of solvent.

6. Any solvent present in the distilled gases from the depolymerization should be separable from the styrene monomer by a separation process such as fractional distillation, to permit production of commercial quality styrene monomer, and reclaimed "styrene oil" mixture for recycling in the depolymerization process.

7. The solvent should not react chemically with polystyrene, or any of the other constituents of napalm.

8. If the solvent deteriorates or decomposes with continued use, the products of decomposition should either be acceptable constituents of the salable end products, or else should be easily removable from the end products.

9. The solvent should be non-toxic, safe to use, and preferably inexpensive.

It has been found that the "styrene oil" mixture that is the result of incomplete depolymerization of polystyrene is actually an ideal solvent for the depolymerization of polystyrene, and particularly for the depolymerization of polystyrene in napalm. The "styrene oil" mixture produced according to the method of the invention satisfies all of the above requirements for a solvent for the process, and greatly simplifies the distillate separation process, as it introduces no new or additional compounds into the depolymerization process. Other solvents with similar properties could also be introduced into the depolymerization process. For example, one or a mixture of a subset of the approximately 20 organic compounds forming the "styrene oil" mixture which may only be produced in small quantities by the polystyrene depolymerization process could be provided and introduced in a suitable quantity to serve as a solvent as well, and recovered and recycled from the "styrene oil" mixture end products. Other solvents or solvent mixtures that meet the above requirements may also be suitable for use in the process of the invention.

Figure 1:
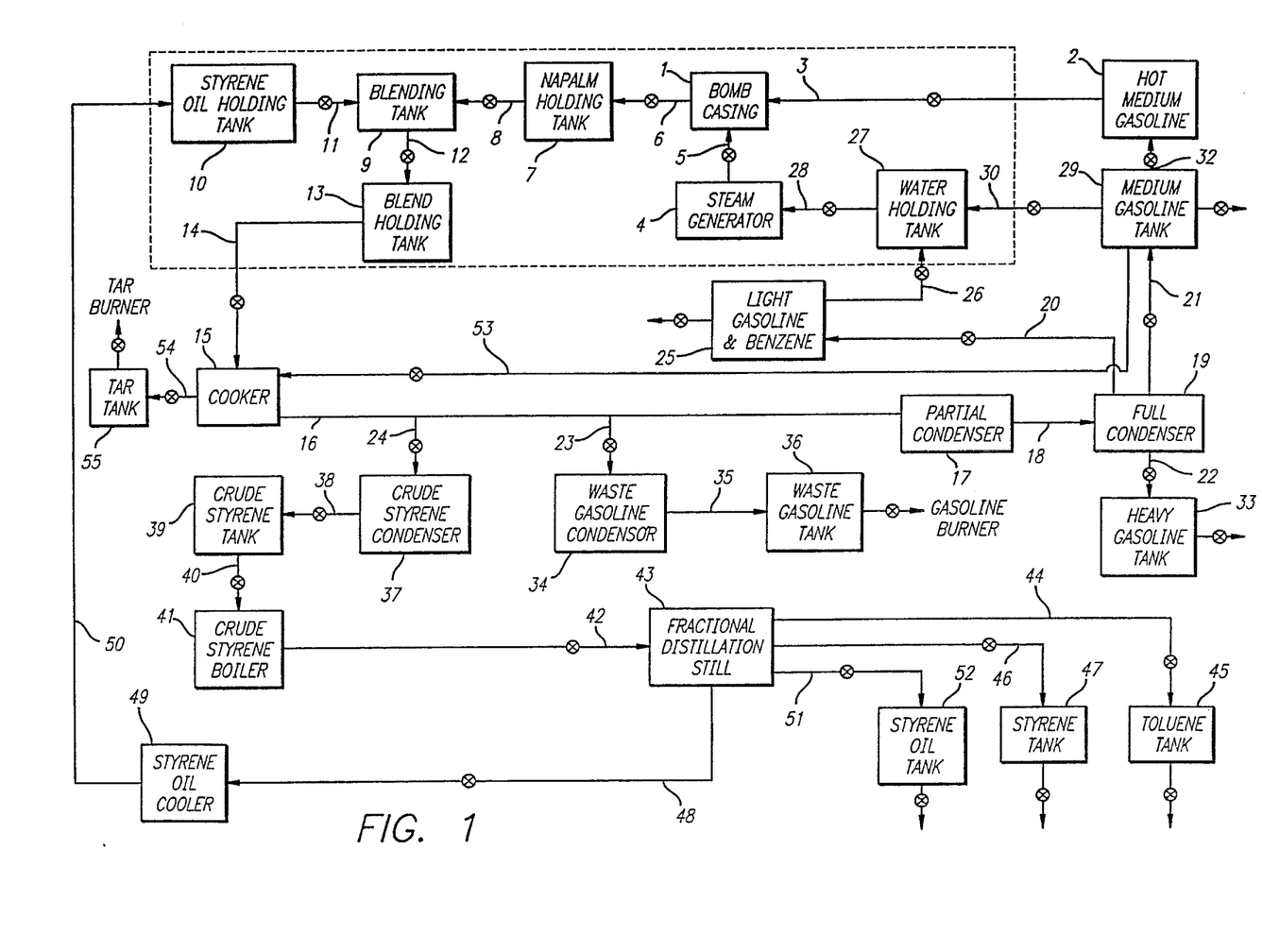
FIG. 1 is a schematic flow diagram of a first preferred embodiment of the method of the invention, as applied to reclamation of napalm.

With specific reference to the process of the invention as applied to reclaiming styrene monomer and other materials from the polystyrene present in napalm, as is illustrated in FIG. 1, the napalm is first removed from the bomb casings 1 by means of hot medium gasoline 2 and steam (generated at 4) through pipes 3 and 5, as previously described. The mixture of napalm, medium gasoline, and water from the casings is led through line 6 to a napalm holding tank 7 for use as required. It is then pumped through line 8 into the blending tank 9, where it is mixed with "styrene oil" solvent previously stored in tank 10, and then pumped through line 11 as required. The napalm is mixed in a ratio from approximately 1/2:1 to 2/3:1 of "styrene oil" to napalm, by weight.

Alternatively, other solvents with suitable properties, such as one or a mixture of a subset of the several organic compounds which comprise the "styrene oil" mixture mentioned above, could be mixed with the napalm at this stage. The solvent greatly reduces the viscosity of napalm at all temperatures present throughout the entire process, which preferably takes place at about atmospheric pressure. Venting of gases to the atmosphere is controlled to prevent pollution, as will be explained later. The blended mixture is then pumped through line 12 into the blend holding tank 13 to await further processing.

Figure 2:
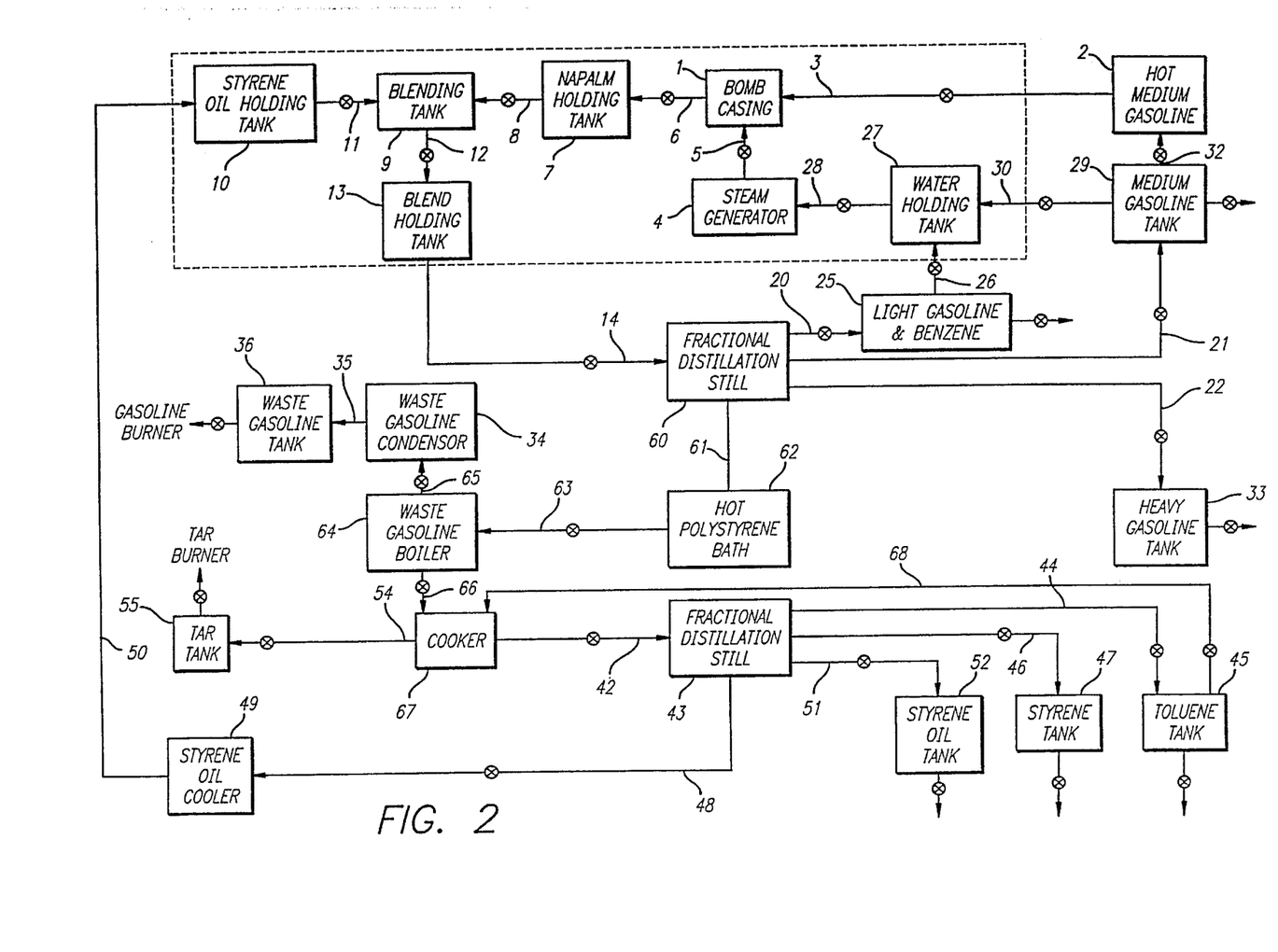
FIG. 2 is a schematic flow diagram of a second preferred embodiment of the method of the invention, as applied to reclamation of napalm.

At this point, there are two alternative processing paths possible, a batch process and a continuous process. Each process has advantages and disadvantages. The currently preferred batch process is simpler to follow step-by-step, so it will be explained first with reference to FIG. 1. It requires cheaper capital equipment and is more adaptable to an intermittent supply of raw material, but has a slower production rate, higher labor cost, and produces lower quality products. The currently preferred continuous process, as shown in FIG. 2, is more sophisticated, has a much higher production rate, and produces higher quality products. It requires more expensive equipment, however, and is intolerant of long interruptions in operation.

Returning to the batch process of FIG. 1, the blended napalm/"styrene oil" mix is pumped through line 14 into the cooker 15, where it is distilled and depolymerized as a batch. For safety reasons, the temperature of the cooker should be less than 50° C. before the napalm is introduced. At the start of cooking a batch, the valves in lines 21, 22, 23, and 24 are closed, and the valves in lines 16 and 20 are open. The partial condenser 17 is not operating (cooling), but the full condenser 19 is operating. The temperature of the contents of the cooker 15 is gradually raised until the refluxing temperature of the distilled vapors at the bottom of the refluxing line 16 reaches about 90° C., during this time the vapors of benzene, water, and light gasoline fractions are being distilled. These vapors pass through line 16, the partial condenser 17, and line 18 into the full condenser 19, where they are completely condensed to liquids. These liquids pass through line 20 to the light gasoline/benzene tank 25. With time, the liquid water settles to the bottom of tank 25, where it is periodically drained through line 26 into water holding tank 27. As liquid water is required for steam generation at 4, it is pumped in through line 28. The light gasoline/benzene mix is drawn periodically from tank 25 for sale.

When the reflux temperature of the vapors reaches 90° C., the partial condenser 17 is gradually brought into operation, initially condensing approximately 10% by weight of the vapors ascending in reflux line 16 and returning them to the cooker down through line 16. As the temperature rises through the collection of the three gasoline fractions, this refluxing is increased to approximately 50% at the end of the collection of heavy gasoline. This partial refluxing is done to keep "styrene oil" from reaching the full condenser 19. The "styrene oil" would be a contaminant in the gasoline which would reduce its sale value, as well as a contaminant in the empty bomb casings, since it would not be evaporated by steam. The remaining lighter vapors in the partial condenser 17 pass through line 18 and are condensed to liquids in the full condenser 19.

Returning to the collection of light gasoline, when the reflux temperature of the vapors reaches 130° C., at which point the temperature of the liquid in the cooker would be about 190° C., the valve in line 21 is opened and the valve in line 20 is closed. The condensed liquid now passes through line 21 into the medium gasoline holding tank 29. With time, any liquid water which might be present settles to the bottom of tank 29, where it is periodically drained through line 30 into the water holding tank 27. The medium gasoline is drawn through line 32 into the hot medium gasoline tank as required for bomb casing cleaning. Surplus medium gasoline is drawn periodically from holding tank 29 for sale.

The temperature of the cooker is raised further, and when the refluxing temperature of the vapors in the partial condenser 17 reaches 150° C., at which point the temperature of the liquid in the cooker would be about 240° C., the valve in line 22 is opened and the valve in line 21 is closed. The vapors are condensed to liquid in the full condenser 19. This liquid passes through line 22 into the heavy gasoline tank 33, from which it is drawn periodically for sale.

When the temperature of the liquid in cooker 15 reaches the highest temperature at which no styrene is produced, about 290° C., at which point the reflux temperature of the partial condenser would be about 175° C., the valve in line 23 is opened and valve in line 16 is closed. The temperature of the cooker 15 is then raised to about 350° C. During this time, the last of the heavy gasoline, which has a boiling point (at about atmospheric pressure) of about 175° C. to 200° C., boils out of the cooker and the polystyrene depolymerization begins, producing styrene and "styrene oil", which contaminate the heavy gasoline. These mixed vapors are diverted into the waste gasoline condenser 34 through lines 16 and 23, and condensed to a liquid, which is then pumped through line 35 into waste gasoline tank 36. The contaminated heavy gasoline is drawn as required to be burned in a gasoline type burner which provides heat to operate the process. After about 5% of the polystyrene has depolymerized, the styrene so produced has swept out enough heavy gasoline from the cooker to reduce the remaining heavy gasoline to an acceptably low level.

The valve in line 24 is then opened and the valve in line 23 is closed. On continued cooking, the vapors of styrene and other styrene-based compounds are produced in cooker 15, and pass through lines 16 and 24 into the crude styrene condenser 37, where they are condensed to a liquid. The liquid passes through line 38 into the crude styrene holding tank 39, where it is stored until required. Heating of the liquid in the cooker is preferably continued at a temperature of about 350° C. until only a small amount of liquid polystyrene remains, to avoid the formation of char in cooker 15. The cooker is then cleaned and cooled in preparation for the next batch of napalm blend, as will be described later.

At this point, the "batch process" is forced to make use of a piece of continuous flow equipment, a state of the art fractional distillation still, in order to achieve the required accuracy of separation between the compounds present in the crude styrene mix. Such a "change of gears" can be accomplished if the crude styrene holding tank 39 is large enough to act as a buffer, perhaps aided by the use of more than one cooker working in alternate time phasing. A steady, continuous flow of crude styrene liquid is pumped through line 40 into the crude styrene boiler 41, which is held at about 325° C., where it is again vaporized and passed through line 42 into the fractional distillation still 43. The top of the still is held at about 145° C. and the bottom of the still is about 325° C. A small amount of a polymerization inhibitor is introduced into still 43 to inhibit any spontaneous repolymerization of the styrene fraction.

The "fractional distillation still" 43 preferably comprises an assembly of two or three fractional distillation columns. The first, with temperatures held at about 145° C. at the top and 325° C. at the bottom, separates a toluene/styrene mixture from the "styrene oil". The second distillation column, with temperature held at about 110° C. at the top and 145° C. at the bottom, separates the toluene from the styrene. Should any significant impurities exist with boiling points between 150° C. and 250° C. which would be harmful to gasoline, a third column can be used to separate these impurities from the "styrene oil" that will be recycled for use in future napalm processing. The toluene (approximately 3% of the original polystyrene) passes through line 44 into the toluene tank 45 for sale, the styrene (approximately 67% of the original polystyrene) passes through line 46 into the styrene tank 47 for sale, and the heavier remaining mix of several compounds, which we have called "styrene oil" (approximately 30% of the original polystyrene) passes through line 51 into the "styrene oil" tank 52. Some of the "styrene oil" is drawn off through line 48 into a cooler 49, where its temperature is reduced for safety to 50° C., and then sent through line 50 to the "styrene oil" holding tank 10 for reuse in the process. The surplus "styrene oil" in tank 52 can either be used as a fuel to operate the process, or sold as a boiler fuel. All of the products of still 43 are condensed to liquids either in the still, if so equipped, or in separate dedicated condensers (not illustrated) which are placed in the outlet lines. Line 51 is placed slightly above the bottom of the still to avoid as much solid inhibitor and polystyrene as possible. These contaminants may interfere with burning the "styrene oil", but do not degrade its use as a napalm solvent. The commercially pure toluene and styrene are, of course, valuable market commodities. The styrene monomer end product was tested for the presence of benzene, and with a sensitivity of 0.1%, no benzene was found in the styrene monomer distillate.

One process remains, cleaning out the cooker 15. At the end of every batch, a small amount of liquid is left in the cooker to avoid the formation of char, which would occur if the cooker 15 were allowed to run dry. This liquid is mostly polystyrene dissolved in "styrene oil", but contains some dissolved styrene monomer which should not be allowed to contaminate the gasoline in the next batch. Cooker 15 is cooled to 120° C., and a small amount of medium gasoline is introduced into the cooker through line 53. The valve in line 23 is opened, and the valve in line 53 is closed. Cooker 15 is boiled vigorously for a few minutes to purge the scavenged styrene monomer vapor into the waste gasoline condenser 34 through lines 16 and 23. It has been estimated that one pound of medium gasoline will be sufficient to clean about twenty pounds of cooker liquid. For safety reasons, the cooker should then be cooled to below 50° C. before introducing a new batch of blended napalm.

In addition, solid impurities must be removed which collect on the bottom of the cooker from several sources: occasional dirt from the napalm, solid lead or lead compounds from the tetraethyl lead and sulfur compounds in the original gasoline, and roughly 1% of a tar produced during the depolymerization of the polystyrene. Fortunately, this tar is completely soluble in hot medium gasoline, and so at the end of every fifth to tenth batch the small amount of medium gasoline introduced into the cooker 15 is first refluxed at its boiling point for a few minutes to dissolve the tar. The medium gasoline is then boiled vigorously as before to purge any remaining styrene monomer into the waste gasoline condenser 34. Finally, the contents of the cooker are dumped down the drain 54 into the tar tank 55. Since this slurry contains lead, it can be separately distilled to remove the nontoxic volatiles and the residue disposed of as toxic waste, or smelted to recover the lead if desired. The cooker is then cooled to below 50° C. for safety as before.

A special safety problem is presented by maintaining the napalm reclamation system at approximately one atmosphere pressure without venting the system to the ambient atmosphere. In general, each separate loop of the system should be vented to at least one other loop, where such venting can be done safely, and the sale products are not cross-contaminated. This venting procedure is similar to standard practice in many chemical plants, such as oil refineries. For clarity, the vent lines are not shown on FIG. 1. The largest volume changes typically occur at the final delivery tanks for benzene, gasoline, styrene monomer, toluene, and "styrene oil" when these liquids are transferred to a delivery truck or railroad tank car. Mobile petroleum containers are now routinely equipped with vapor transfer systems, however, which move vapor from an empty truck, for example, into the top of a storage tank while liquid is being transferred from the storage tank into the truck. The vapor transfer system helps to prevent gases from the napalm reclamation plant from leaking into the atmosphere, and also helps to maintain the process pressure conditions at one atmosphere. Outflows of gas from the process can be minimized and cleansed by chilling through a refrigerated heat exchanger to condense all but the lowest boiling point components, and by scavenging the remainder with charcoal filters. Inflows of gas to prevent a system vacuum can be provided by supplying nonflammable gas as needed.

An examination of the mechanical and rheological properties of polystyrene produced from the styrene end product of the process of the invention indicates that no significant cross-linking impurities such as divinyl benzene exist in the styrene monomer recovered. However, a trace impurity is present in the styrene product which inhibits spontaneous repolymerization from beginning for approximately two months. This impurity, which does not affect the clarity of the polystyrene produced from the styrene end product, can thus greatly enhance the storage and shipment of styrene monomer. If desired, the trace impurity can easily be removed by washing the styrene with an equal volume of water. There is also a possibility that a small fraction of the chemicals produced during depolymerization may have a boiling point sufficiently close to the boiling point of styrene monomer to require a more careful separation process, such as those conventionally employed in the commercial production of styrene, and such as are well known in the art.

Another preferred embodiment of the napalm reclamation apparatus is illustrated in FIG. 2, which outlines a preferred embodiment of a continuous flow process according to the invention. This process has much in common with the batch process, with the exception of the central distillation and depolymerization equipment. The entire front end of the process, which covers the removal of napalm from the bomb casings, the cleaning of the casings with hot medium gasoline and steam, and the blending of napalm with "styrene oil", or one of its derivatives, is identical to the batch process (Items 1–13). All reference numerals in FIG. 2 which are smaller than 60 are identical with the same equipment illustrated in FIG. 1. Reference numerals greater than 59 identify equipment different from FIG. 1.

Since the unloading of bomb casings is necessarily a "batch process", the napalm/"styrene oil" blend holding tank 13 should be large enough to accept normal variations in the rate of unloading bombs, so that a continuous flow (24 hours a day, 7 days a week) of blend at the desired rate can be delivered through line 14 to the top of the first fractional distillation still 60. The objective of still 60 is to separate the lower boiling point fluids, gasoline, benzene, and water, from the "styrene oil" and dissolved polystyrene.

Since still 60 is standard state of the art equipment, the details of its internal operation will not be covered. Because solid impurities exist in the blend, still 60 must withdraw its output from the mainstream in the form of vapors, which are then condensed to liquids in dedicated condensers. These condensers may be integral with the still, or outside of the still in the output lines, depending on the selected still design. For clarity, these dedicated condensers are not illustrated in FIG. 2. Still 60 receives the energy required for its operation through line 61 from heated bath 62 at its lower end, which contains a mixture of boiling heavy gasoline (about 3% by weight of the liquid in heated bath 62), "styrene oil" and dissolved polystyrene, which is held at 290° C. This temperature level will ensure that no styrene monomer will be formed in hot bath 62 or still 60 to contaminate the gasoline products.

Moving downwards from the top of the still, the first tap delivers a mixture of light liquids with boiling points below 130° C. These liquids include light gasoline, benzene, and water. They are sent through line 20 to the light gasoline/benzene tank 25 where the water settles out and is drawn through line 26 to the water holding tank 27. The gasoline/benzene mixture, freed of water, is drawn off periodically for sale. The second tap delivers liquid medium gasoline, with a boiling point between 130° C. and 150° C., which is sent through line 21 to medium gasoline tank 29. Any water which might have been carried into this tank can settle out and be drained through line 30 into the water holding tank 27. Recirculation of water and medium gasoline to the bomb casing cleaning equipment is provided as in FIG. 1. The excess production of medium gasoline is drawn off periodically for sale. The third tap delivers liquid heavy gasoline with a boiling point from 150° C. to 175° C. (at about atmospheric pressure) through line 22 into tank 33, from which it can be drawn periodically for sale. The polystyrene and "styrene oil" contained in the napalm blend flow out of the bottom of still 60 into the hot bath 62, together with various impurities.

The mixed content of the hot bath 62 is then pumped continuously through line 63 into the waste gasoline boiler 64, where its temperature is raised to approximately 350° C. The heaviest fraction of the gasoline, with a normal boiling point of 175° C. to 200° C., contaminated with a mixture of styrene monomer and "styrene oil" which is produced by depolymerizing about 5% of the polystyrene, boils off; the mixed vapor passes through line 65 to the waste gasoline condenser 34, and then as a liquid through line 35 to the waste gasoline holding tank 36, as in FIG. 1. The waste gasoline is burned to provide heat for the process, as before.

The heavy gasoline content in the hot bath 62 liquid has now been reduced to an acceptably low level. This hot liquid is pumped continuously from waste gasoline boiler 64 through line 66 into the cooker 67, which holds it at a temperature of about 350° C. until the polystyrene substantially completely depolymerizes. The function of cooker 67 is thus analogous to the final depolymerization function of cooker 15 of FIG. 1. The vapor products of depolymerization, together with the vapor of the "styrene oil", pass through line 42 to the second fractional distillation still 43, which separates it into the same liquid outputs which were described in FIG. 1. Some of the "styrene oil" is pumped from the bottom of still 43 through line 48, cooler 49, and line 50 for recirculation to the "styrene oil" holding tank 10 for blending with napalm. Solid impurities remain in cooker 67.

The problem of cleaning the tar and solid residues out of the cooker 67 is more difficult than for cooker 15 of the batch process in FIG. 1. Fortunately, cooker 67 does not have to be cleaned of solid residue very often, a schedule comparable to the fifth to tenth batch of cooker 15. Cooker 67 must be taken off line for a short time to clean it, which interrupts the continuous flow of material through the fractional distillation still assembly 43. By first restricting the material input to cooker 67, it can be nearly emptied, and then cooling is begun, as is done with cooker 15 of FIG. 1 near the end of a batch. As soon as cooker 67 is no longer producing vapor, all valves in the input and outlet lines of still assembly 43 are closed and it is allowed to idle. When cooker 67 has cooled to 100° C., a small quantity of toluene from tank 45 is pumped through line 68 into cooker 67 and refluxed for a few minutes to dissolve the tar. Toluene is used to dissolve the tar instead of the less expensive medium gasoline used in FIG. 1, because the dregs of any medium gasoline introduced into the process at cooker 67 would contaminate the output products of still 43, whereas toluene dregs in cooker 67 are readily separable in still 43.

After the tar is dissolved, the entire contents of cooker 67 are dumped into the tar tank 55 through line 54 and disposed of similarly to the batch process. When cooker 67 has been dumped, refilled, and the production of vapor resumed, the input and output valves of still 43 are reopened and production starts anew. The waste gasoline boiler 64 should be large enough to act as a buffer for the output of still 60 during the cooker 67 clean-out time. It is hoped that the relatively brief delay will not degrade to an unacceptable level the purity of the outputs of still 43 which are produced immediately after restart. If it does, however, the substandard products may be recirculated back into cooker 67, using additional lines not illustrated, for reseparation in still 43 until normal operation of still 43 is achieved.

Figure 3:
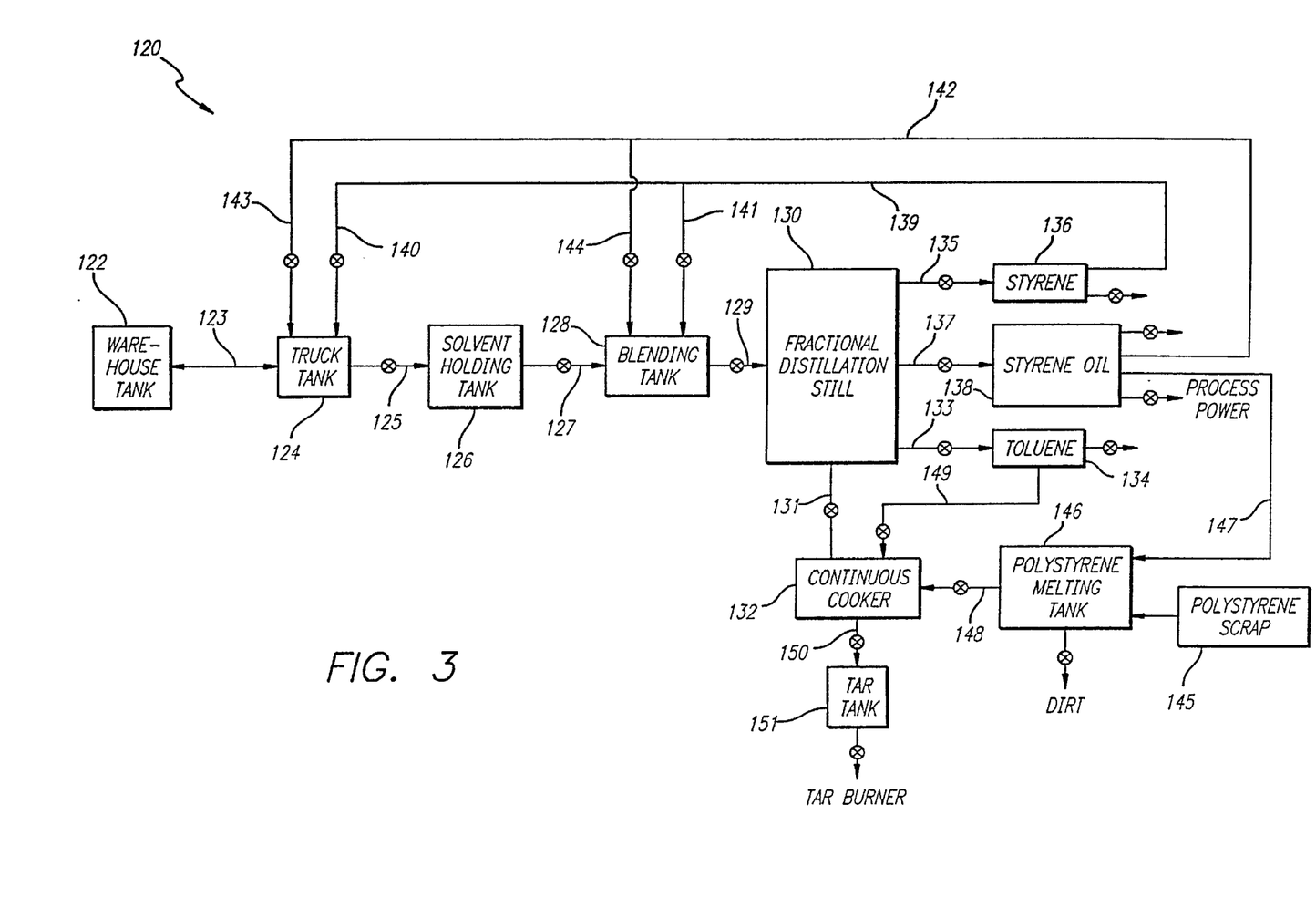
FIG. 3 is a schematic flow diagram of a third preferred embodiment of the method of the invention, as applied to reclamation of polystyrene products.

Now referring to FIG. 3, the process of the invention for processing and reclaiming other types of polystyrene products, and more specifically applied to foamed polystyrene products, will be described. Recalling the manner in which the invention can economically solve the difficult problem of cleaning solidified napalm out of bomb casings by using solvents (steam and medium gasoline) which are regenerated and reused in the process itself, the invention also represents an almost ideal solution to the problem of reclamation of foamed polystyrene, again using materials which can be regenerated and reused in the process itself. Foamed polystyrene readily dissolves in styrene, the "styrene oil" mixture resulting from the incomplete depolymerization of polystyrene (or a similar suitable solvent as described above), and mixtures thereof. All of these solvent combinations can dissolve up to approximately 30 times their own volume of solid foamed polystyrene (and up to 100 times their volume if the foamed polystyrene is loose fill), and still remain suitably fluid for reclamation. Styrene dissolves foamed polystyrene very rapidly, but has a significant odor, and is relatively flammable, having a flash point of about 35° C. The "styrene oil" solvent mixture dissolves foamed polystyrene more slowly, but has little odor and a very high flash point at least above 100° C.

Because of its extremely low density, the transport of polystyrene foam for salvage over distances of only a few miles by truck is an uneconomic activity. The costs of loading, operating the truck, and unloading rapidly consume the salvage value of the very small weight of polystyrene foam material which will fit into a typical truck. These same considerations make polystyrene foam a very unwelcome component of garbage and land fill. The ability of styrene and "styrene oil" to increase the density of polystyrene foam by a factor of 30 to 100 completely alters this problem, and makes the transport of polystyrene foam from a large inhabited area to a central processing plant of economical size a reasonable activity.

In addition to polystyrene foam, solid styrene plastic frequently occurs as industrial scrap, or in garbage. The process shown in FIG. 3 effectively recycles both forms of polystyrene in the same plant. Discarded polystyrene, especially in garbage, is subject to contamination by a wide variety of materials. It is known that some contaminants, such as certain vegetable oils, interfere with satisfactory operation of the invention, and others, such as water or common dirt, do not. Because the effects on the invention process of all possible forms of contamination have not been thoroughly investigated, it is preferable that the polystyrene must be sufficiently "clean" before being processed in order to not interfere substantially with the method of the invention. This requirement places a premium on collecting the discarded polystyrene at its source, before it has been contaminated with unknown materials. It is also possible to remove contaminants from waste polystyrene by washing or other methods, if necessary.

Clean discarded polystyrene foam is generated in many industrial plants and retail stores as a result of unpacking other objects which have been packaged to protect against shipment damage. Referring to FIG. 3, in the polystyrene reclamation system 120, polystyrene, in the form of polystyrene foam and/or small pieces of solid polystyrene, can be introduced into a collection tank 122 which contains styrene monomer, "styrene oil", or mixtures thereof. The undesirable bulk of the discarded polystyrene foam is thus greatly reduced by dissolving at the time of introduction into the tank at the originating site. Many collection tanks can be placed at various warehouses where polystyrene or polystyrene foam is discarded, and a collection truck 124 can either transport the full collection tanks to the processing site, or pump out the contents of the collection tank through a hose 123 into a transporting tank in the truck, and refill the collection tank with the appropriate solvent stored in a second truck tank through the same hose 123. Solvent in the truck tank can be refilled as needed with styrene and "styrene oil" through lines 140 and 143, or with other solvents suitable for on site use. The full collection truck returns to the processing plant and empties its load through hose 125 into a holding tank 126. The solvent supply tank in the truck is then refilled with the desired solvent mix of styrene and/or "styrene oil" from storage tanks 136 and 138, respectively. The supply to tanks 136 and 138 will be described later.

From time to time, warehouse polystyrene solution is pumped from the holding tank 126 through line 127 into the blending tank 128, where it can be blended either with styrene through lines 139 and 141, or with "styrene oil" through lines 142 and 144. The blending adjusts the chemical content and room temperature viscosity of the blended solution to the proper conditions for further processing in a fractional distillation still assembly. A mixture ratio of about 2 parts of styrene and 1 ½ parts of "styrene oil" per 1 part of polystyrene plastic by weight should work well. A continuous flow of blend is then pumped through line 129 into a fractional distillation still assembly 130, which comprises at least two distillation columns. Still assembly 130 operates through line 131 in close conjunction with the continuous cooker 132. The still assembly 130 and cooker 132 combination is somewhat analogous in function to the still assembly 43 and cooker 67 combination illustrated in FIG. 2 for napalm processing, except combination 130/132 operates in a different flow pattern because its input feed is a relatively low temperature liquid blend containing water as a contaminant. This feed cannot be introduced directly into cooker 167 safely, but must be introduced into the much cooler top of still assembly 130.

The first distillation column in still assembly 130 operates between about 100° C. at its upper end and approximately 350° C. in the cooker 132 at its lower end. Depolymerization of polystyrene occurs continuously in the cooker at about 350° C. The mainstream works its way down through the first still 130, and vapors of water, toluene, styrene, and some "styrene oil" leave the first still to enter the second still, which is more closely analogous to the first still of still assembly 43. Melted polystyrene, "styrene oil", and solid impurities flow through line 131 into the cooker 132, where depolymerization occurs. The vapors of these depolymerization products migrate back into the first still 130 where they also exit to the second still. From this point, the second and third stills perform the same separation of the distillates as still assembly 43 of FIG. 2. Toluene, contaminated with a little pure water, is tapped off through line 133 into toluene tank 134. Commercially pure styrene, possibly contaminated with a little pure water, is tapped off through line 135 into styrene tank 136, and "styrene oil" is tapped off through line 137 into the "styrene oil" tank 138. The water contaminant in the toluene and styrene separates as a liquid phase by gravity, and is drained away as in FIG. 1. The drainage is not recirculated, but is cleaned of all hydrocarbon dregs in a charcoal filter and discarded. The solid impurities collect in cooker 132. In general, the previous descriptive comments concerning the operation of still 43 and cooker 67 therefore also apply to still 130 and cooker 132.

If a significant source of solid polystyrene scrap is to be processed, it can be treated most efficiently by avoiding the step of room temperature dissolving in a solvent, since it does not have the bulk density problem of polystyrene foam. Solid polystyrene scrap 145 is introduced into a heated batch melting tank 146, together with the proper amount of "styrene oil" from tank 138 through line 147 to maintain proper viscosity of the melt. When the mix of melted polystyrene and "styrene oil" has reached the proper temperature and viscosity, it is pumped at a modest continuous rate through line 148 into the cooker 132, where it joins the main stream of processing. Any "clean" dirt from the scrap polystyrene will settle to the bottom of the melting tank 146, where it can be diluted with a little toluene or "styrene oil" for mobility, and drawn off to be discarded or burned for its heat content. Unless unusual conditions exist in the scrap, this dirt is not toxic waste.

As in cooker 67 of FIG. 2, tar is formed in cooker 132 as a byproduct of depolymerization, and the inevitable dirt will also collect. The cooker must be cleaned periodically, as is cooker 67, to remove the tar and other dirt which may be present. The procedure of idling the still, cleaning the cooker using toluene through line 149, and restarting the still is the same for cooker 132 in FIG. 3 as it is for cooker 67 in FIG. 2. The tar and dirt are dumped through line 150 into the tar tank 151 for later disposal. Unlike the processing of napalm, the tar and dirt from polystyrene scrap processing is probably not toxic waste, as there is no lead in polystyrene scrap.

Some of the "styrene oil" can be burned to provide heat for the entire recycling process, along with the tar and toluene wash. Excess toluene, the styrene, and excess "styrene oil", a useful boiler fuel and possibly a Diesel engine fuel, can be sold commercially.

The basic process of the invention produces roughly 70% styrene and 30% "styrene oil" by depolymerization of polystyrene. However, it has been found by experiment that the output of "styrene oil" can be altered as a percentage of the total polystyrene both by the use of catalysts, and by varying the rate of depolymerization with time. Manganese oxide and copper are two such effective catalysts, and many other materials are probably also effective catalysts. By the use of appropriate catalysts and process conditions, the production of styrene monomer can be increased to nearly 100%, and the production of "styrene oil" can be reduced to nearly 0%, as desired. Such a goal may be desirable in a processing plant after sufficient "styrene oil" has been produced to serve as the required "solvent working capital", if a fuel cheaper than the value of "styrene oil" or its equivalent in styrene is available to provide the process energy requirements.

It will be apparent from the foregoing that while particular forms of the invention have been illustrated and described, various modifications can be made without departing from the spirit and scope of the invention. Accordingly, it is not intended that the invention be limited, except as by the appended claims.

What is claimed is:

1. A method for reclamation of styrene from polystyrene in polystyrene based products, comprising the steps of:

mixing the polystyrene based product with a solvent to form a polystyrene solution having a sufficiently low viscosity to allow free boiling of said polystyrene solution, said solvent being selected from the group consisting of vinylbenzene, and styrene oil resulting from the partial depolymerization of polystyrene, said styrene oil having a pour point below −20° C. and a boiling point between about 300° C. and 320° C.;

heating the polystyrene solution to a temperature of from approximately 300° C. to 400° C. to depolymerize the polystyrene and to produce a vinylbenzene fraction and a heavier containing said styrene oil as a result of the partial depolymerization of polystyrene;

separating the vinylbenzene fraction from the heavier fraction; and recycling at least a portion of said styrene oil to provide at least a portion of said solvent in the step of mixing said polystyrene with said solvent to form a polystyrene solution prior to said step of heating the polystyrene solution.

2. The method of claim 1, wherein said step of separating the vinylbenzene fraction from the heavier fraction comprises heating the vinylbenzene fraction and the heavier fraction to a temperature of from about 145° C. to about 325° C. to distill the vinylbenzene and heavier fractions; and separating the vinylbenzene fraction from the heavier fraction by continuous fractional distillation.

3. The method of claim 2, wherein said vinylbenzene fraction includes toluene, and said step of separating the vinylbenzene fraction from the heavier fraction comprises distilling said vinylbenzene, said toluene and said heavier fraction by continuous fractional distillation.

4. A method for reclamation of vinylbenzene from polystyrene based products, comprising the steps of:

mixing the polystyrene based product with a solvent selected from the group consisting of vinylbenzene, and styrene oil resulting from the partial depolymerization of polystyrene, said styrene oil having a pour point below −20° C. and a boiling point between about 300° C. and about 320° C., and mixtures thereof, to form a polystyrene solution having a sufficiently low viscosity to allow free boiling of said polystyrene solution;

heating the polystyrene solution to a temperature of from about 300° C. to about 400° C. to depolymerize the polystyrene and to produce a vinylbenzene fraction and a heavier fraction of partial depolymerization products containing said styrene oil as a result of the partial depolymerization of polystyrene;

separating the vinylbenzene fraction from the heavier fraction by continuous fractional distillation; and recycling at least a portion of said styrene oil to mix with said polystyrene in forming said polystyrene solution.

5. The method of claim 4, wherein said vinylbenzene fraction includes toluene, and said step of separating the vinylbenzene fraction from the heavier fraction comprises heating the vinylbenzene fraction and the heavier fraction to a temperature of about 110° C. to about 325° C. to distill said vinylbenzene, said toluene and said heavier fraction by continuous fractional distillation.

6. A method for reclamation of styrene from polystyrene in polystyrene based products, comprising the steps of:

mixing the polystyrene based product with a solvent selected from the group consisting of vinylbenzene and a mixture of vinylbenzene with styrene oil resulting from the partial depolymerization of polystyrene, said styrene oil having a pour point below −20° C. and a boiling point between about 300° C. and about 320° C., to form a polystyrene solution having a sufficiently low viscosity to allow free boiling of said polystyrene solution;

heating the polystyrene solution to a temperature of from about 300° C. to about 400° C. to depolymerize the polystyrene and to produce a vinylbenzene fraction and a heavier fraction containing said styrene oil as a result of the partial depolymerization of polystyrene;

separating the vinylbenzene fraction from the heavier fraction by continuous fractional distillation; and recycling at least a portion of said styrene oil to mix with said polystyrene in forming said polystyrene solution prior to said step of heating the polystyrene solution.

* * * * *